(12) United States Patent
Hopfauf et al.

(10) Patent No.: US 7,374,422 B2
(45) Date of Patent: May 20, 2008

(54) PROCESS AND KIT FOR PRODUCING A DENTAL RESTORATION PIECE

(76) Inventors: Simonette Hopfauf, Bagoltenweg 6, A-6845 Hohenems (AT); Volker Rheinberger, Mareestrasse 34, FL-9494 Vaduz (LI)

( * ) Notice: Subject to any disclaimer, the term of this patent is extended or adjusted under 35 U.S.C. 154(b) by 317 days.

(21) Appl. No.: 10/753,187

(22) Filed: Dec. 31, 2003

(65) Prior Publication Data

US 2005/0048441 A1    Mar. 3, 2005

(30) Foreign Application Priority Data

Aug. 26, 2003  (DE)  ................................ 103 39 246

(51) Int. Cl.
*A61C 13/00* (2006.01)
*A61C 13/08* (2006.01)

(52) U.S. Cl. ......................................... 433/206; 264/16

(58) Field of Classification Search ............ 433/201.1, 433/202.1, 223, 206–208; 427/2.1; 520/109, 520/113, 120
See application file for complete search history.

(56) References Cited

U.S. PATENT DOCUMENTS

| | | | | |
|---|---|---|---|---|
| 2,192,902 A | * | 3/1940 | Erdle | ........................... 264/18 |
| 3,052,982 A | * | 9/1962 | Weinstein et al. | ........... 433/206 |
| 3,786,565 A | * | 1/1974 | Jarrault | ..................... 433/200.1 |
| 4,104,798 A | | 8/1978 | Takahashi et al. | |
| 4,431,451 A | * | 2/1984 | Mabie et al. | ................... 106/35 |
| 4,497,629 A | * | 2/1985 | Ogino et al. | ............. 433/201.1 |
| 4,557,691 A | * | 12/1985 | Martin et al. | ............. 433/199.1 |
| 4,585,417 A | * | 4/1986 | Sozio et al. | .............. 433/202.1 |
| 4,806,383 A | * | 2/1989 | Poltz | ........................... 427/2.27 |
| 4,812,120 A | * | 3/1989 | Flanagan et al. | ........... 433/173 |
| 4,818,559 A | * | 4/1989 | Hama et al. | ................ 427/2.27 |
| 4,834,651 A | * | 5/1989 | Fenick | ........................... 433/74 |
| 4,879,136 A | * | 11/1989 | Polz | ........................... 427/2.27 |
| 4,917,347 A | * | 4/1990 | Fenick | ........................ 249/54 |
| 4,957,440 A | * | 9/1990 | Hankins et al. | ........... 433/201.1 |
| 5,852,248 A | * | 12/1998 | Chadwick | ..................... 75/228 |
| 6,206,958 B1 | | 3/2001 | Panzera et al. | |
| 6,426,149 B1 | * | 7/2002 | Machida | ..................... 428/434 |
| 6,534,197 B2 | * | 3/2003 | Noda et al. | ................. 428/689 |

FOREIGN PATENT DOCUMENTS

| | | |
|---|---|---|
| DE | 37 13919 A1 | 11/1988 |
| DE | 82 27 782.6 U1 | 5/1989 |
| DE | 92 04 832.3 U1 | 7/1992 |

* cited by examiner

*Primary Examiner*—John J Wilson
(74) *Attorney, Agent, or Firm*—John C. Thompson; Alan S. Kosman

(57) ABSTRACT

A process is provided for producing a dental restoration piece that has a frame with first and second portions and a blended synthetic material covering a first portion of the frame, the heat expansion coefficient of the blended synthetic material being different than the heat expansion coefficient of the frame material. Prior to a thermal treatment of the dental restoration piece, at least the second portion of the frame is covered with a heat protection paste, whereby the heat protection paste limits the increase in temperature of the frame resulting from thermal treatment of the dental restorative piece to effect curing of the blended synthetic material to a lesser temperature value than if the heat protection paste had not been applied onto the dental restorative piece. Also disclosed is a kit for practicing the process.

14 Claims, 4 Drawing Sheets

PROCESS AND KIT FOR PRODUCING A DENTAL RESTORATION PIECE

CROSS-REFERENCE TO RELATED APPLICATIONS

This application claims foreign priority benefits under 35 U.S.C. §119(a)-(d) from German patent application ser. no. P 103 39 246.7 filed Aug. 26, 2003.

TECHNICAL FIELD

The present invention relates to a process and kit for producing a dental restoration piece, and more particularly to a process for making a dental restoration piece which includes a frame and a blended synthetic material covering a first portion of the frame, characterized by prior to a thermal treatment of the dental restoration piece, covering at least a second exposed portion of the frame with a heat protection paste.

BACKGROUND OF THE INVENTION

A dental restoration piece-producing process typically provides for the use of two materials. Frequently, blended synthetic materials are applied to metal frames in order to make possible an aesthetically satisfactory dental restoration piece and to increase the biological compatibility of the dental restoration piece.

Blended synthetic materials are typically cured or hardened into a cured condition via irradiation thereof with light or heat or via a combination of light and heat. This results in an increase in temperature of the material. Problems then arise due to the difference between the heat expansion coefficients of the blended synthetic materials which have been applied onto metal frames and the heat expansion coefficient of the metal of the metal frames. While the blended synthetic material is typically still soft during the heating up phase—namely, in connection with a positive temperature gradient, the blended synthetic material hardens during the cooling off phase, whereupon stresses occur for the reason that the synthetic material contracts more than the metal during the cooling off phase.

Since the heat expansion coefficient of blended synthetic material is greater, hairline cracking occurs in the blended synthetic material either immediately after the polymerization, after the completion of production, or, possibly, also occasionally after the passage of a certain amount of time following production. Such cracking can lead to the accumulation of bacteria in usage.

Aside from the adverse hygienic considerations, another problem is that the collective securement of the blended synthetic material on the dental restoration piece is degraded by such stress cracking so that the danger exists that a portion of the blended synthetic material comes loose. Typically, the stress relief occurs as well at the thinnest locations of the dental restoration piece—for example, at interdental locations.

It has already been suggested, in order to prevent such problems, to accommodate or align the heat expansion coefficient of the synthetic material to the greatest extent possible to that of the deployed metal coatings. This approach, however, is subject to physical limitations as well as the functional requirement that polymeric synthetic materials must typically be deployed of the type which are curable via light and/or heat irradiation.

It has been suggested, in fact, to apply a compensation layer on the metal frame before the blended synthetic material is applied thereunto with the objective that the compensation layer will elastically or resiliently yield such that the occurrence of stress cracking in the contracting blended synthetic material will be avoided.

Such solutions are, however, technically problematical to realize in practice, are expensive, and, moreover, are apt to degrade the securement or attachment of the blended synthetic materials.

OBJECTS AND SUMMARY OF THE INVENTION

The present invention provides a solution to the challenge of providing a process for producing a dental restoration piece which offers an improved long-term stability without hygienic or securement problems in connection with two-layer dental restoration pieces.

The inventive solution provides that portions of the metal frame have a heat protection paste applied thereunto. The heat protection paste forms an insulation for the particularly good heat conducting metallic regions. Upon heating up via convection or radiation heat, as is typically provided, the metal frame is heated less strongly than the blended synthetic material, due to the deployment of the heat protecting paste. The temperature difference can amount to, for example, 40° C., such temperature difference being dependent upon the particular region of the blended synthetic material which is measured. Via this measure, it is ensured that the stresses on the border surfaces between the metal and the synthetic material are lower. Titanium has, for example, a linear heat expansion coefficient of $8.35 \times 10-6$ per degree. In contrast, many synthetic materials have linear heat expansion coefficients of 50 to $100 \times 10-6$ per degree.

The heat protection paste can advantageously comprise approximately 60% water, approximately 20% di-ethylene glycol, as well as approximately 1% high-temperature resistant or stable fibers, and, additionally, suitable heat-resistant fillers.

It is to be understood that, in accordance with the present invention, the thickness of the heat protection paste can be accommodated over a wide range of applications to the respective requirements—that is, to the requirement of the required reduction of the temperature level needed to make ready a stress-free hardening. If a maximum temperature of 70° C. in lieu of a maximum temperature of 110° C. is to be achieved on the outer surface of the metal frame, the deployment of a material thickness of 2 mm of a commercially available heat protection paste is sufficient, such as SR Adoro ThermoGuard available from Ivoclar Vivadent AG.

In accordance with the present invention, it is particularly advantageous that the metal has a comparatively high heat capacity. During the heating up phase, which can amount to, for example, 10 minutes, the metal frame is indeed heated up via the atmospheric air even though the metal frame is covered by the heat protection paste. Via the heat insulation provided by the heat protecting paste, however, the heating up of the metal frame is less intense so that the peak temperature toward the end of the heating up phase is always at a temperature such as, for example, 30° C., which is lower than the temperature of the atmospheric air.

By means of the heat protection paste that remains at the dental restoration piece after firing, it is possible to achieve a long-term cooling outside the furnace, i.e. the heat protection paste prevents the entire restoration piece or sections thereof, respectively, from rapidly cooling down. The long-term cooling is effected by the furnace and the temperature in the furnace chamber is lowered time-controlled. The long-term cooling requires approximately 15 minutes which can be saved by using the heat protection paste.

Further advantages, details, and features are described in the hereinafter following description of an embodiment of the present invention with reference to the drawings.

DETAILED DESCRIPTION OF THE PREFERRED EMBODIMENT

In a comparison experiment, a dental restoration piece was subjected to a typical polymerization process which provided a combination of light and heat irradiation to effect hardening of the polymer, the hardening also being referred to as curing.

The dental restoration piece indicated generally at 10 is comprised of a metal frame 12 having first and second portions 12a and 12b, respectively, and a blended synthetic material 14 which partially covered the first portion of the metal frame. A dental polymer based on polymethyl methacrylate was deployed as the blended synthetic material.

Figure 1:
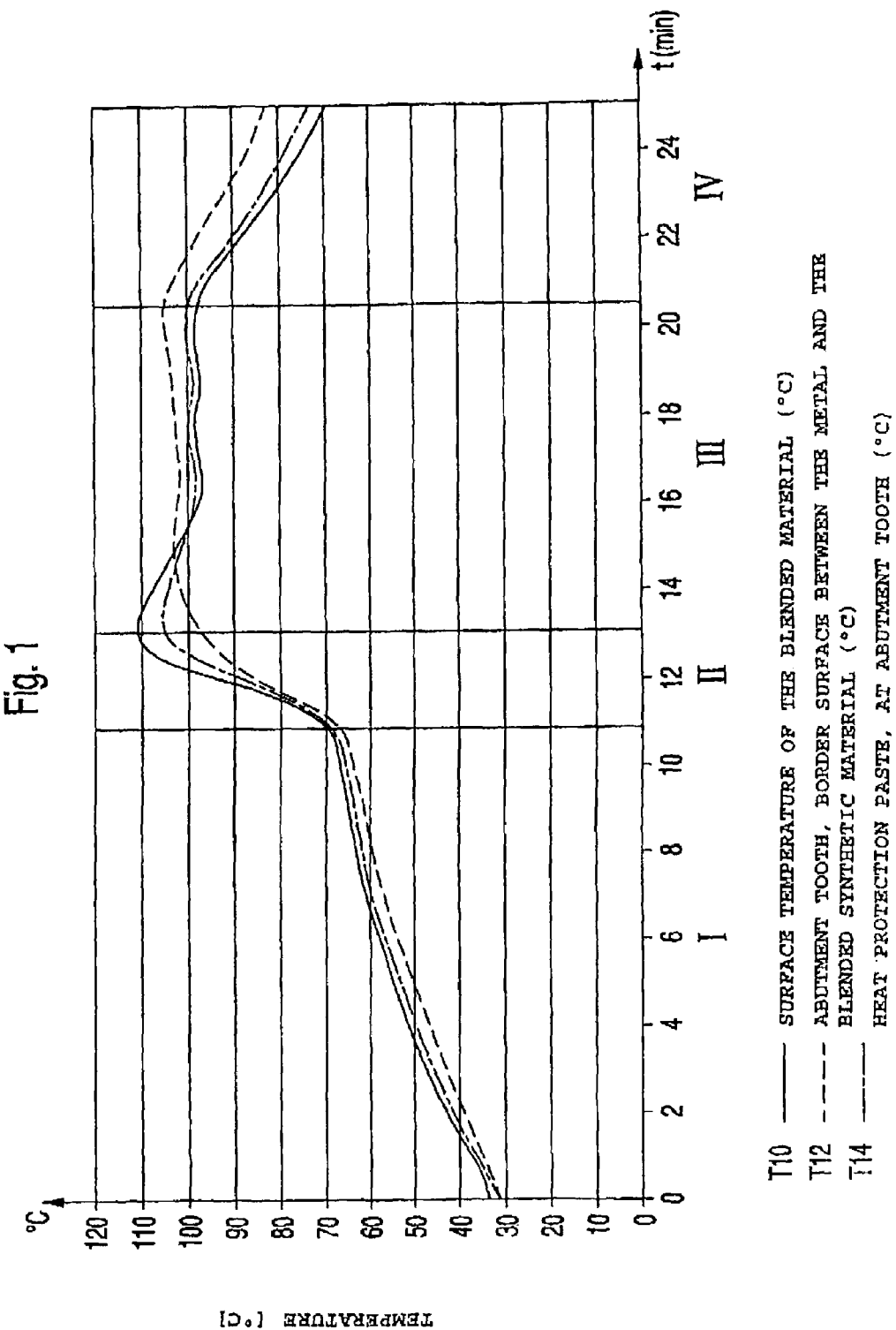
FIG. 1 is a graphical representation of the temperature path of a four-member dental restoration bridge without the use of the inventive heat protecting paste.
Figure 2:
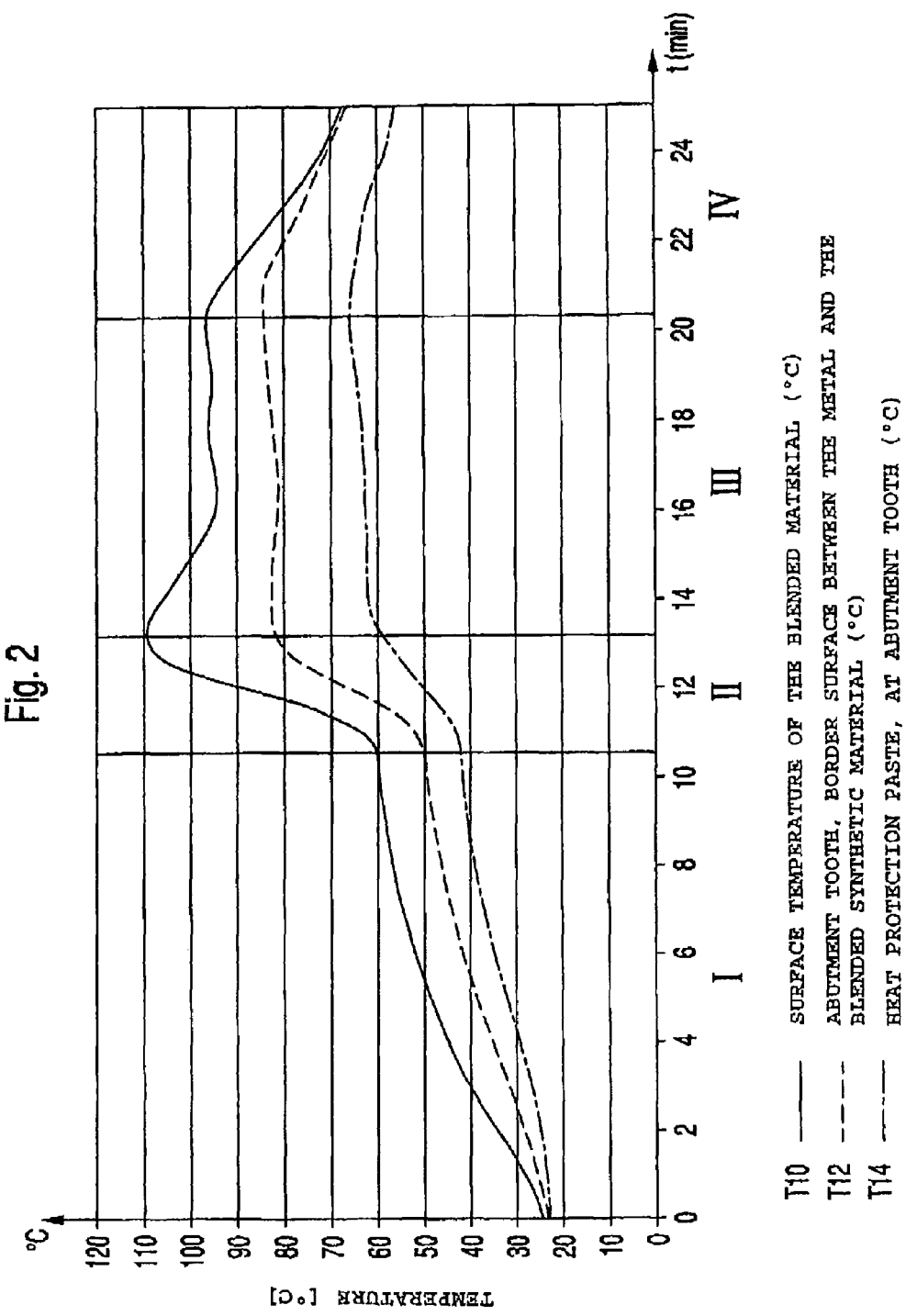
FIG. 2 is a graphical representation of a temperature path similar to that shown in FIG. 1 but, however, showing the temperature path of a dental restoration bridge which has had the inventive heat protection paste applied thereon.
Figure 3:
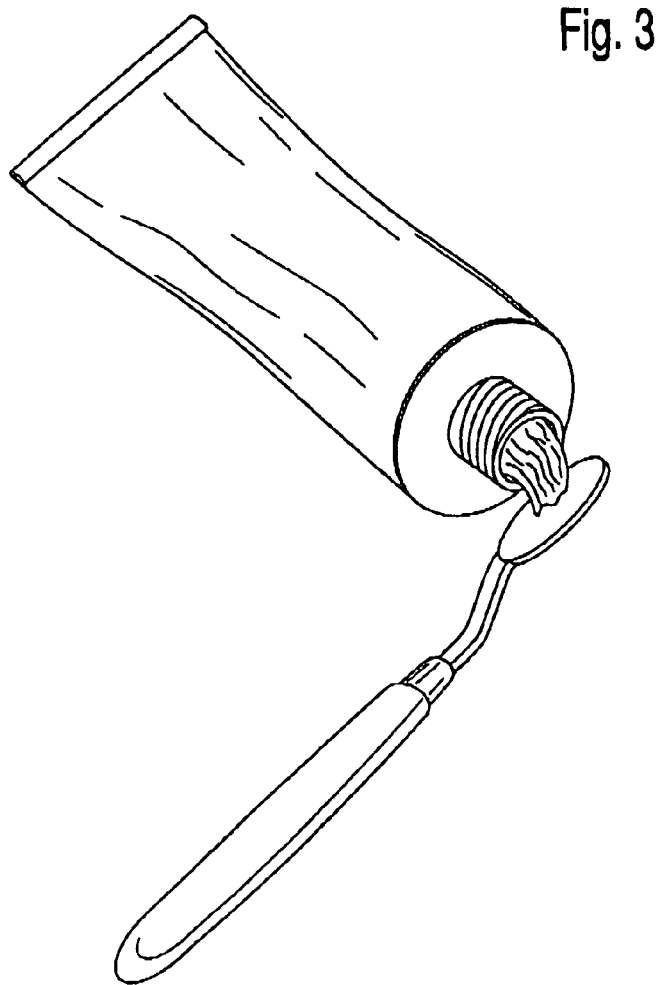
FIG. 3 illustrates a kit for applying a heat protection paste onto a dental restoration piece, the kit in this embodiment including a tube of heat protection paste and a an applicator configured like a spatula.
Figure 4:
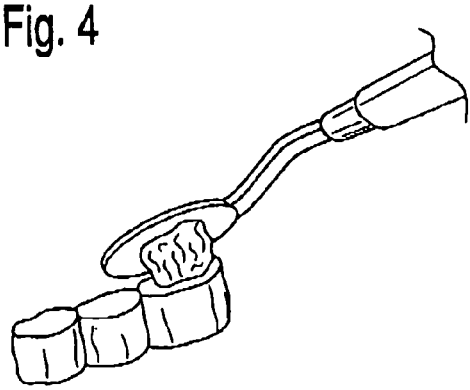
FIG. 4 illustrates the spatula of FIG. 3 applying a heat protection paste onto a dental restoration piece.
Figure 5:
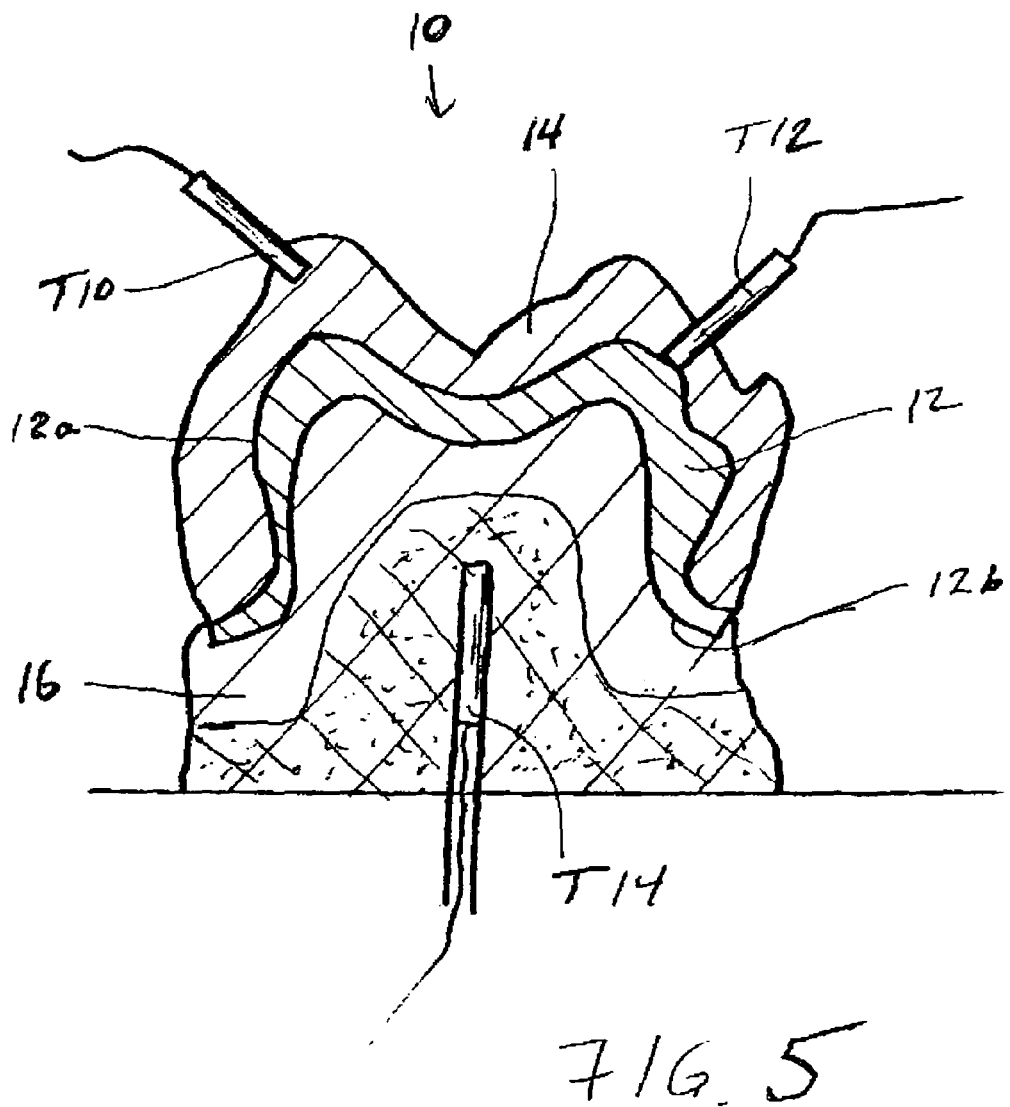
FiG. 5 illustrates the metal frame having first and second portions and a blended synthetic material covering the first portion, and a heat protection paste covering the second portion of the frame.

During a light phase I, which is graphically represented in FIG. 1, the dental restoration piece was subjected to light irradiation. In this connection, the outer surface temperature T1O of the blended synthetic material—that is, the atmospheric temperature—was measured as well as the temperature T12 at an abutment tooth, which is a tooth for the support thereon of a bridge or other dental restorative structure, and specifically at the border surfaces between the metal and the blended synthetic material.

Moreover, the temperature T14 was measured on the abutment tooth itself which was free of any blended synthetic material application thereon.

The output temperatures at the beginning of the light phase I were as follows:
T10: 34° C.
T12: 32° C.
T14: 32° C.

T10 is normally the room temperature; otherwise, T10 is the operational temperature of the oven in a condition of the oven with an open cover.

A heating up phase II was performed following the light phase I and, subsequent thereto, the temperature was held to slight fluctuations during the heating up phase III and, subsequently, cooling off occurred during the cooling off phase IV.

The following temperatures were measured at the end of the relevant phases:

| Measurement Location | Light Phase I | Heating Up Phase II | Heating Up Phase III | Cooling Off Phase IV |
|---|---|---|---|---|
| T10 | 68 C. | 112 C. | 98 C. | 70 C. |
| T12 | 67 C. | 97 C. | 107 C. | 86 C. |
| T14 | 68 C. | 105 C. | 101 C. | 74 C. |

A similarly configured dental restoration piece was then provided with a heat protection paste 16 covering the second portion of the metal frame in accordance with the inventive process. The deployed heat protection paste was of the type SR Adoro ThermoGuard .

The next-following table sets forth the respective temperatures measured with respect to the deployment of the dental restoration piece with a heat protection paste thereon, whereby the same reference temperatures are provided as were described in connection with FIG. 1:

| Measurement Location | Light Phase I | Heating Up Phase II | Heating Up Phase III | Cooling Off Phase IV |
|---|---|---|---|---|
| T10 | 60 C. | 109 C. | 96 C. | 67 C. |
| T12 | 50 C. | 82 C. | 85 C. | 68 C. |
| T14 | 42 C. | 59 C. | 66 C. | 57 C. |

It can be seen that the temperature T14—that is, the temperature of the metal frame which is covered by the heat protection paste, lie significantly under the temperature of the metal frame that was measured in connection with the dental restoration piece, whose measured temperatures are plotted in FIG. 1, which did not have a heat protection paste thereon.

The heat protection paste is, after cooling off phase of the dental restoration piece, mechanically removed from and/or washed off the dental restoration piece. A visual confirmation confirmed that the tendency towards stress cracking is clearly reduced.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A process for producing a dental restoration piece, the dental restoration piece including a metal frame having first and second portions and a blended synthetic material covering the first portion, whereby the heat expansion coefficient of the blended synthetic material differs from the heat expansion coefficient of the frame material, said process comprising:

prior to a thermal treatment of the dental restoration piece, covering the entirety of an exposed region of the frame with a heat protection paste; and subsequently thermally treating the dental restoration piece, wherein the deployment of the heat protection paste reduces the temperature which the frame reaches on account of the heating up phase by at least 20° C. as compared to the peak temperature that the frame would otherwise be subjected to if the heat protection paste were not so deployed.

2. A process according to claim 1, wherein the heat expansion coefficient of the blended synthetic material is a selected one of greater or smaller than the heat expansion coefficient of the frame material.

3. A process according to claim 1, wherein the thermal treatment of the dental restoration piece includes hardening of the blended synthetic material and a thereafter following cooling off of the blended synthetic material, and the heating up of the blended synthetic material during the thermal treatment is effected via radiation heat or convective heat.

4. A process according to claim 1, wherein the thermal treatment includes heating up of the dental restoration piece from a location exteriorly of the dental restoration piece.

5. A process according to claim 1, wherein the blended synthetic material and the heat protection paste together cover and encase the frame.

6. A process according to claim 1, wherein the blended synthetic material is a material curable into a hardened condition by at least one of the dual application of pressure and heat, the application of heat, and the irradiation thereof with light.

7. A process according to claim 1, wherein at least part of the blended synthetic material is a ceramic material.

8. A process according to claim 1, wherein the material of the frame is a selected one of a metal and a metal coating.

9. A process according to claim 1, wherein the heat protection paste has a layer thickness of 0.5 to 2 mm.

10. A process according to claim 1, wherein the heat protection paste is, after its deployment during the thermal handling of the dental restoration piece, mechanically removed from and/or washed off the dental restoration piece.

11. A process according to claim 1, wherein the heat protection paste comprises at least water, di-ethylene glycol, and high-temperature resistant fibers.

12. A process according to claim 1, wherein the heat protection paste comprises filler material and layered silicate and/or color material.

13. A process according to claim 1, wherein the heat protection paste comprises polyethylene glycol.

14. A process for producing a dental restoration piece, the dental restoration piece including a metal frame having first and second portions and a blended synthetic material covering the first portion, whereby the heat expansion coefficient of the blended synthetic material differs from the heat expansion coefficient of the frame material, said process comprising:

prior to a thermal treatment of the dental restoration piece, covering the entirety of an exposed region of the frame with a heat protection paste; and subsequently thermally treating the dental restoration piece, wherein the thermal conductivity coefficient of the heat protection paste is less than 0.1 W/cm ° C.

* * * * *